(12) United States Patent
Hidalgo et al.

(10) Patent No.: US 7,357,561 B2
(45) Date of Patent: Apr. 15, 2008

(54) EVAPORATOR DEVICE FOR ACTIVE SUBSTANCES WITH AN INCORPORATED LIGHT

(75) Inventors: Joan Gusi Hidalgo, Barcelona (ES); Ruben Garcia Fabrega, Barcelona (ES); Andrea Caserta, Barcelona (ES)

(73) Assignee: Zobele Espana, S.A., Barcelona (ES)

( * ) Notice: Subject to any disclaimer, the term of this patent is extended or adjusted under 35 U.S.C. 154(b) by 535 days.

(21) Appl. No.: 10/982,529

(22) Filed: Nov. 5, 2004

(65) Prior Publication Data
US 2005/0133617 A1    Jun. 23, 2005

Related U.S. Application Data

(63) Continuation of application No. PCT/ES02/00211, filed on May 6, 2002.

(51) Int. Cl.
*F21V 33/00* (2006.01)
(52) U.S. Cl. .................. 362/643; 362/96; 362/101; 362/642; 392/392; 392/395
(58) Field of Classification Search .................. 362/95, 362/96, 101, 641, 642, 643, 644; 392/392, 392/395
See application file for complete search history.

(56) References Cited

U.S. PATENT DOCUMENTS 6,236,807 B1 *   5/2001   Ruffolo et al. .............. 392/390
6,859,615 B2 *   2/2005   Yip et al. .................... 392/395
2005/0053368 A1*  3/2005  Pesu et al. ................... 392/390

FOREIGN PATENT DOCUMENTS

| EP | 0976410 A1 | 2/2000 |
| ES | 2137111 A1 | 12/1999 |
| ES | 2163956 B2 | 5/2003 |
| WO | WO 01/19416 A1 | 3/2001 |
| WO | WO 01/68154 A1 | 9/2001 |

OTHER PUBLICATIONS

International Search Report for International Application No. PCT/ES 02/00211 dated Jul. 11, 2002.

* cited by examiner

*Primary Examiner*—Laura Tso
(74) *Attorney, Agent, or Firm*—Knobbe, Martens, Olson & Bear

(57) ABSTRACT

The device forms a single unit that includes the way by which the evaporation of active substances is achieved, as well the way that allows automatically lighting a small lamp or LED that emits a small light illuminating the container of the active substance to be evaporated. This allows one to see the contents in the dark and, in addition, constituting a light in the dark for the area surrounding the device, with the particularity that the volume of this device does not increase with respect to the devices meant to individually evaporate active substances and emit a light. The design of the device includes a general casing comprising a pinholder body for a plug and the container itself for the active substance, in such a way that the body incorporates a sensor that emits a signal for the automatic activation of the lamp or illumination LED when the light intensity is below a pre-established threshold.

12 Claims, 4 Drawing Sheets

EVAPORATOR DEVICE FOR ACTIVE SUBSTANCES WITH AN INCORPORATED LIGHT

CROSS REFERENCE TO RELATED APPLICATION

This application claims priority under 35 U.S.C. § 120 to PCT International Application Number PCT/ES02/00211 filed on May 6, 2002 and not published in the English language. The disclosure of the above-described filed application is hereby incorporated by reference in its entirety.

BACKGROUND

1. Field of the Invention

The present invention relates to a device for evaporating active substances with an incorporated light. The invention has various aspects, certain ones of which will be discussed below.

2. Description of the Related Technology

A type of device or apparatus connectable to the power grid to produce the evaporation of volatile products or active substances is known. These devices, regardless of their design and different embodiments, present as a common factor the inclusion of a casing that includes the pinholder body for electrical connection, in addition to being provided with the adequate means to adaptedly support the corresponding container of the product or active substance that must be evaporated. These devices are also provided with a heating element, preferably comprised of electrical resistances or of another suitable component that heats a wick that is submerged in the product meant to evaporate and emerges from the opening of the container, so that the substance or product reaching the outer and emergent length of this wick by capillarity vaporizes due to the heat produced by the heater.

On the other hand, at times this type of devices is accompanied by an electronic circuit that allows regulating the power of the heating element and thus the evaporation level; this electronic circuit can be embodied as a printed circuit that may even carry out other functions, as well as constituting the means for joining the plug pins directly by soldering.

Devices of the abovementioned type are also known with other means to regulate the rate of the evaporation of the product or active substance; these regulatory means can be based on positioning the heating element at a greater or lesser distance from the wick by relative displacement between the heating element and the container.

Spanish invention patent P9801793 of the same applicant describes a means to regulate the rate of evaporation based on an axially-displaceable bushing disposed between the outlet orifice of the device and the heating element, this bushing forming part of an arm that ends at an appendix guided inside an inclined groove established for this purpose in the outer casing of the device, in such a way that the displacement in either direction of the appendix through the length of the inclined groove is accompanied by the upward or downward axial displacement of the bushing, determining in the first case a continuous neck between the exit orifice and the heating element that acts as a chimney to aid evaporation, while in the second case the bushing distances itself from the exit orifice and is placed so that it envelopes the wick interposed between such wick and the heating element, thereby hindering the evaporation level of the product.

Devices are also known that are connected to the power grid, as the aforementioned devices, and incorporate a small lamp or LED that turns on and emits a small light in the darkness, for use in baby and/or children's rooms to avoid total darkness and allow the baby or child to perceive a degree of clarity.

DESCRIPTION OF CERTAIN INVENTIVE ASPECTS

The invention has various aspects, certain ones of which will be discussed below. A single unit allows a dual function of the device which, on one hand, evaporates the active substance and, on the other, illuminates the container holding that substance, allowing its level to be known in the dark as well as emitting a dim light providing a dimly lit view of the surroundings of the device.

Certain aspects of the invention provide a technical solution which will allow uniting the two functions in a single device, so that this device works as an evaporator of active substances or volatile products and as a lighting device, also being applicable to the field of devices which provide or emit a small light that can be used, for example, in baby or young children's rooms. This type of device operates by connecting it to the electrical grid.

The proposed device has been conceived to achieve the integration in a single device which allows it to function simultaneously as an evaporator and to emit a small light, without this entailing an increase in volume or complexity with respect to single-function conventional instruments.

Based on these characteristics, the device embodiments present the particularity of incorporating an electronic circuit to which the plug pins are connected and to which the heating element is connected, as well as a lamp or LED associated with automatic activation circuit. This activation occurs when a sensor located in the pinholder body detects a low lighting intensity, that is, when the ambient lighting decreases below a pre-established threshold.

Another characteristic of device embodiments is the incorporation of a transparent casing between the container holding the product or active substance to be evaporated and the pinholder body, the transparent casing acting as a medium to diffuse the light towards the container so that its content level can be known in the darkness.

This transparent casing furthermore protects the active parts of the electronic circuit, being mounted on a support and placed between the pinholder body and the general casing acting as a cover for the internal structure of the device, on whose support the heating element is adaptedly fitted, although this heating element as well as the regulator are adaptedly mounted on a support casing provided in the interior of the device, specifically between the support of the transparent casing and the general casing acting as a lid, the lower part of that support-casing being placed over the upper part of the transparent casing.

Embodiments of the apparatus thus constructed present a size no greater than that of an apparatus intended for evaporation only, with the particularity that the light it emits is enough for the light to be catalogued as a night light in addition to it constituting a light indicator for the container of the volatile product or active substance.

Furthermore, the different parts and/or above described components of embodiments of the device are designed to allow a simple assembly, enabling its automation.

BRIEF DESCRIPTION OF THE DRAWINGS

As a complement of the description being made and in order to aid a better understanding of the characteristics of the invention, in accordance with an example of a preferred embodiment, a set of drawings is accompanied as an integral part of the description where for purposes of illustration only and in a non-limiting sense the following is shown.

DESCRIPTION OF CERTAIN INVENTIVE EMBODIMENTS

Figure 1:
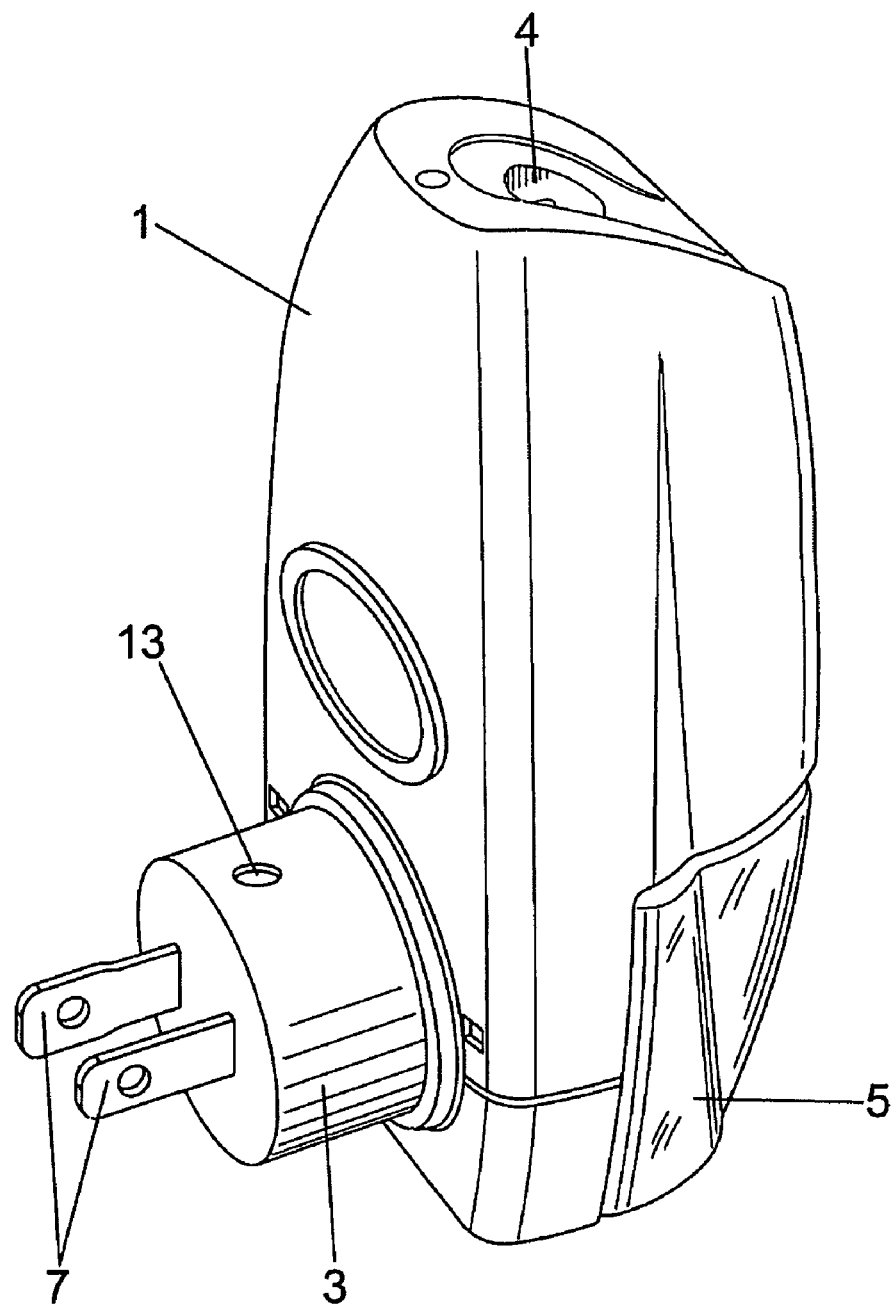
FIG. 1 is a perspective view of an embodiment of the device of the invention, on the side on which the plug pinholder body is located.
Figure 2:
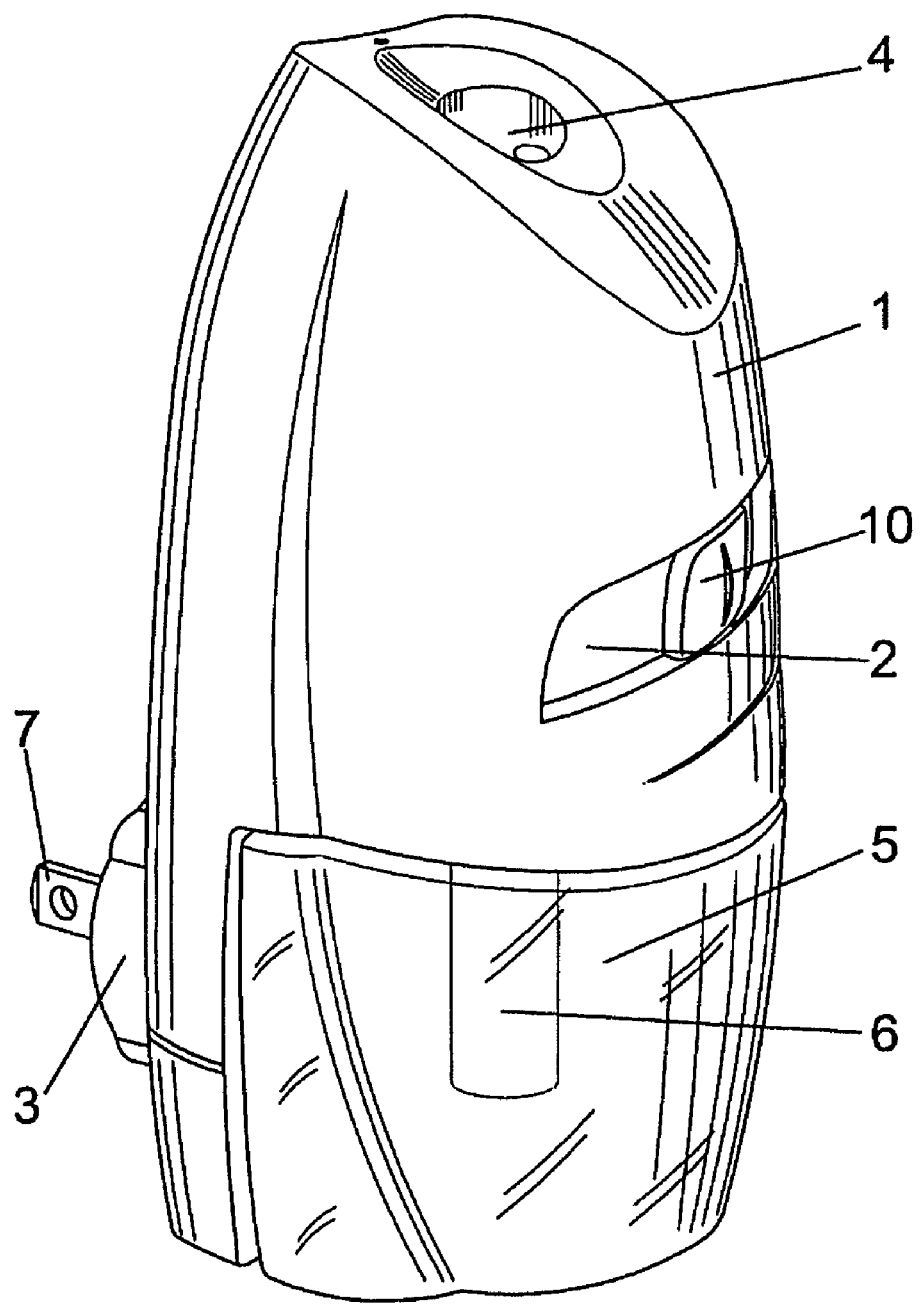
FIG. 2 is another view, also in perspective, of the same device, in this case of the side corresponding to the active substance container vision, as well as of the manually activated appendix for regulating evaporation rate.
Figure 3:
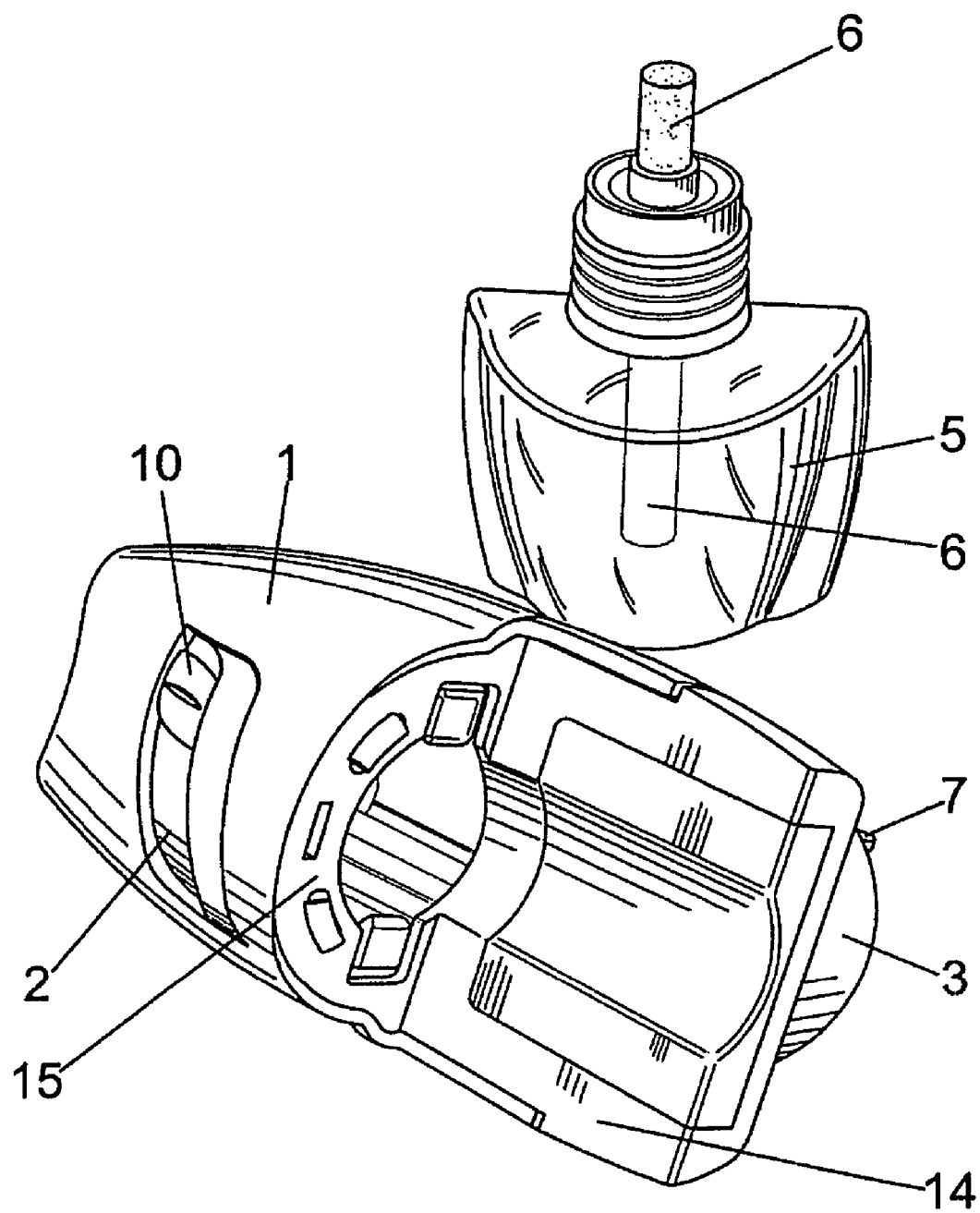
FIG. 3 is a perspective view of the apparatus and container of the active substances separately, where the device support on which the container is positioned and secured can be seen.

In view of the above-described drawings, it can be seen that an embodiment of the device comprises a general casing (1) acting as a cover, with a inclined groove whose function will be explained hereinafter, and in the upper end an outlet orifice (4) for the active substance which evaporates and that is held in a container (5) through the opening of which emerges a length of wick (6) that is submerged inside the content or active substance of the container (5), all of which is complemented by a body (3) that holds the corresponding plug pins (7).

Figure 4:
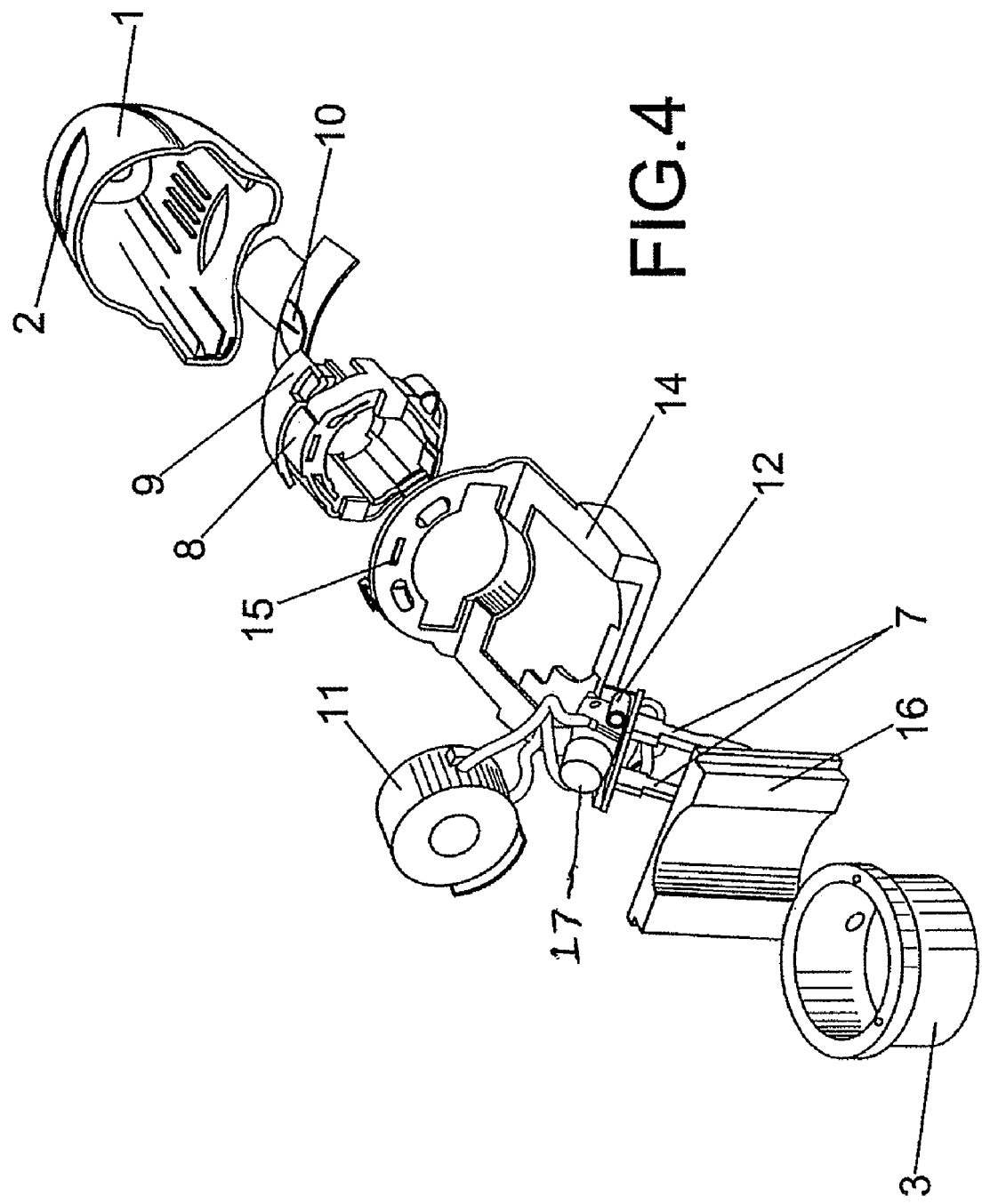
FIG. 4 is an exploded perspective view of the different elements or parts which make up the device embodiment, without the container of the active substance.

The device is also provided with an evaporation rate regulator (9), which, as seen in FIG. 4 is connected to adjustor element (10), which protrudes into hole (2) of the general casing (1).

The heating element (11) is connected to an electronic circuit or electronic unit (12) to which the plug pins (7) are preferably joined by soldering, although they may be connected to the electronic circuit (12) in a different way. This circuit also feeds a lamp or LED (17) which automatically activates by way of the signal received by a sensor (13) located on the body (3) of the plug pins (7). Thus, when the sensor (13) detects a low light level, i.e. a level below the pre-established threshold, it emits the corresponding signal to the electronic circuit (12) so that the lamp automatically activates. This emits a dim light that on the one hand illuminates the container (5), allowing one to view the level of active substance contained in it in the darkness, and on the other hand provides night illumination, or at least emits a small light in the darkness.

The active substance container (5) is duly supported and adjusted on a support (14) provided in correspondence with the lower part of the casing (1), support (14) which has an upper part (15) on which is positioned and adjusted the heating element (11), which in turn is adjusted, together with the bushing (8) of the evaporation rate regulator, in the part (15) of the support (14).

A transparent casing (16) has also been provided between the container (5) and the pinholder body (3). This transparent casing (16) acts as a diffuser so that the light is directed toward the container (5), and also as protection for the active parts of the electronic circuit (12).

Thus, inventive aspects relate to a device that provides a technical constructive solution such that it carries out two different functions, one of them consisting of evaporating the active substance held in the container (5) and the other consisting of emitting a small light, functions which are currently performed by separate apparatuses.

Thus, embodiments of the device provide an apparatus that, without increasing the size of the conventional and independent apparatuses that evaporate volatile substances and emit light, carries out these two functions based on a series of parts whose shape and design characteristics, such as are shown in FIG. 4, allow a quick and easy assembly that even enables an automation of this assembly.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. The scope of the invention is indicated by the appended claims rather than by the foregoing description. All changes which come within the meaning and range of equivalency of the claims are to be embraced within their scope.

What is claimed is:

1. An evaporator device for active substances with an incorporated light, of the type comprising:
    a casing with a pinholder body for connection to the power grid, on which casing a container is duly supported and adjusted a container for the active substance to be evaporated, from which container emerges a wick that is heated by a heating element placed directly in front of it, also including an evaporation rate regulator and being of the type that includes a single electrical unit configured to produce the evaporation of the active substance and to light a small lamp or LED,
    wherein the device further comprises a transparent casing placed between the container of the active substance and the pinholder body, constituting a medium that diffuses light towards the container allowing a view of the contents of the container in the dark and illuminating the surroundings of the device, as well as a protection for the active ports of the electronic circuit.

2. The evaporator device for active substances with an incorporated light as claimed in claim 1, wherein the pinholder body of the plug incorporates a low-light detection sensor that sends a suitable signal and automatically produces the lighting of the small lamp or LED.

3. The evaporator device for active substances with an incorporated light as claimed in claim 1, further comprising an electronic circuit to which are soldered the respective plug pins as well as the connections of the lamp or illumination LED and the connections of the corresponding heating element.

4. The evaporator device for active substances with an incorporated light as claimed in claim 1, further comprising a casing-support that, in addition to being configured to adapt and secure the active substance container, constitutes an assembly and adaptation medium for both the heating element and the bushing corresponding to the evaporation rate regulator, such that the casing-support constitutes in turn the adapted assembly medium for the transparent casing.

5. The evaporator device for active substances with an incorporated light as claimed in claim 1, wherein the corresponding general casing constitutes a protective cover for the internal structure of the device.

6. An evaporator device for active substances with an incorporated light, comprising:
- a casing with a pinholder body for connection to the power grid;
- a container for the active substance to be evaporated, wherein the container is duly supported and adjusted on the casing;
- a wick emerging from the container;
- a heating element placed directly in front of the wick and configured to heat the wick;
- an evaporation rate regulator positioned between an outlet orifice of the casing and the heating element;
- a single electrical unit being configured to produce the evaporation of the active substance and to light a small lamp or LED; and
- a transparent casing placed between the container of the active substance and the pinholder body, constituting a medium that diffuses light toward the container, thereby allowing a view of the contents of the container in the dark and illuminating the surroundings of the device, as well as protection for the active ports of the electronic circuit.

7. The evaporator device of claim 6, wherein the pinholder body of the plug comprises a low-light detection sensor configured to send a signal and thereby automatically produce the lighting of the small lamp or LED.

8. The evaporator device of claim 6, further comprising an electronic circuit, wherein two or more plug pins, connections for the lamp or illumination LED, and connections for the heating element are soldered to the electronic circuit.

9. The evaporator of claim 6, further comprising a casing-support configured to adapt and secure the active substance container, wherein the casing-support comprises an assembly and adaptation medium for both the heating element and a bushing corresponding to the evaporation rate regulator.

10. The evaporator device of claim 6, wherein the casing comprises a protective cover for the internal structure of the device.

11. An evaporator device for active substances, comprising:
- means for connection to the power grid;
- means for containing an active substance to be evaporated;
- means for supporting and adjusting the containing means;
- means for heating a wick emerging from the containing means;
- means for regulating an evaporation rate of the active substance positioned proximal to the heating means;
- means for evaporating the active substance and lighting a small lamp or LED; and
- means for diffusing light toward the containing means, placed between the containing means and the connection means, thereby allowing a view of the contents of the container in the dark and illuminating the surroundings of the device, as well as protection for active ports of the evaporating and lighting means.

12. The evaporator device of claim 11, further comprising means for sensing a low-light condition and sending a signal to the lighting means.

* * * * *